United States Patent
Popoff et al.

(10) Patent No.: US 10,377,727 B2
(45) Date of Patent: Aug. 13, 2019

(54) PROCESS FOR THE PREPARATION OF GAMMA-VALEROLACTONE

(71) Applicant: Synvina C.V., Amsterdam (NL)

(72) Inventors: Nicolas André Vélu Popoff, Amsterdam (NL); Jan Cornelis van der Waal, Amsterdam (NL)

(73) Assignee: Synvina C.V., Amsterdam (NL)

( * ) Notice: Subject to any disclaimer, the term of this patent is extended or adjusted under 35 U.S.C. 154(b) by 0 days.

(21) Appl. No.: 15/765,738

(22) PCT Filed: Oct. 6, 2016

(86) PCT No.: PCT/NL2016/050692
§ 371 (c)(1),
(2) Date: Apr. 4, 2018

(87) PCT Pub. No.: WO2017/061865
PCT Pub. Date: Apr. 13, 2017

(65) Prior Publication Data
US 2018/0290993 A1    Oct. 11, 2018

(30) Foreign Application Priority Data

Oct. 6, 2015  (NL) .................................... 2015578

(51) Int. Cl.
| | |
|---|---|
| *C07D 307/02* | (2006.01) |
| *C07D 307/33* | (2006.01) |
| *B01J 21/04* | (2006.01) |
| *B01J 21/06* | (2006.01) |
| *B01J 21/08* | (2006.01) |
| *B01J 21/12* | (2006.01) |
| *B01J 23/04* | (2006.01) |
| *B01J 23/72* | (2006.01) |
| *B01J 23/755* | (2006.01) |
| *B01J 23/80* | (2006.01) |
| *B01J 23/89* | (2006.01) |

(52) U.S. Cl.
CPC ............ *C07D 307/33* (2013.01); *B01J 21/04* (2013.01); *B01J 21/063* (2013.01); *B01J 21/066* (2013.01); *B01J 21/08* (2013.01); *B01J 21/12* (2013.01); *B01J 23/04* (2013.01); *B01J 23/72* (2013.01); *B01J 23/755* (2013.01); *B01J 23/80* (2013.01); *B01J 23/892* (2013.01); *B01J 23/8966* (2013.01)

(58) Field of Classification Search
CPC .... C07D 307/33; C07D 315/00; B01J 23/892; B01J 23/72; B01J 23/8966; B01J 23/80; B01J 23/755; B01J 23/04; B01J 21/04; B01J 21/063; B01J 21/066; B01J 21/08; B01J 21/12
USPC .................................................. 549/295, 326
See application file for complete search history.

(56) References Cited

U.S. PATENT DOCUMENTS

| | | |
|---|---|---|
| 2,786,852 A | 3/1957 | Dunlop et al. |
| 4,420,622 A | 12/1983 | van de Moesdijk et al. |
| 6,617,464 B2 | 9/2003 | Manzer |
| 7,935,834 B2 | 5/2011 | Bhattacharyya et al. |
| 8,003,818 B2 | 8/2011 | Van Den Brink et al. |
| 8,598,303 B2 | 12/2013 | Castelijns et al. |
| 8,598,372 B2 | 12/2013 | Hwang et al. |
| 8,975,421 B2 | 3/2015 | Rode et al. |
| 2007/0208183 A1 | 9/2007 | Haan et al. |
| 2011/0046399 A1 | 2/2011 | Haan et al. |
| 2012/0302764 A1 | 11/2012 | Dumesic et al. |
| 2013/0296579 A1* | 11/2013 | Rode .................... C07D 307/33 549/326 |

FOREIGN PATENT DOCUMENTS

| | | |
|---|---|---|
| JP | 2014-166604 A | 9/2014 |
| WO | 2005/058793 A1 | 6/2005 |
| WO | 2006/067171 A1 | 6/2006 |

OTHER PUBLICATIONS

Lv, Jinkun, et al., "Highly efficient conversion of bio-mass derived levulinic acid into γ-valerolactone over Ni/MgO catalyst", RSC Adv. 2015 5:72037-72045.

\* cited by examiner

*Primary Examiner* — Taylor V Oh
(74) *Attorney, Agent, or Firm* — Hoffmann & Baron, LLP

(57) ABSTRACT

Gamma-valerolactone is prepared from a levulinic acid ester in a continuous process where a stream of the levulinic acid ester together with a gaseous stream of a hydrogen-containing gas is contacted with a hydrogenation catalyst, where the levulinic acid ester is in the liquid phase, and where the hydrogenation catalyst is a solid particulate catalyst including at least one hydrogenating metal, supported on an oxide carrier.

19 Claims, No Drawings

PROCESS FOR THE PREPARATION OF GAMMA-VALEROLACTONE

CROSS-REFERENCE TO RELATED APPLICATIONS

This application is the National Stage of International Application No. PCT/NL2016/050692, filed Oct. 6, 2016, which claims the benefit of Netherlands Application No. NL 2015578, filed Oct. 6, 2015, the contents of which is incorporated by reference herein.

FIELD OF THE INVENTION

The present invention relates to a process for the preparation of gamma-valerolactone. In particular it relates to a process for the preparation of gamma-valerolactone from an ester of levulinic acid.

BACKGROUND OF THE INVENTION

Gamma-valerolactone (GVL), i.e. 5-methylbutyrolactone or 5-valerolactone, is a chemical compound that can for instance be used as a precursor in the manufacture of adipic acid, i.e. 1,6-hexanedioic acid. Adipic acid and 1,6-hexanediamine are the monomers in the preparation of polyamides, viz. nylon-6,6. Further, adipic acid can be used in the production of polyurethanes. Esters of adipic acid can be used as plasticizers, e.g. in PVC. Other applications of adipic acid include its use as gelling agent in foods and as ingredient in controlled release medicines.

Adipic acid may be produced from GVL by converting GVL to pentenoic acid or a pentenoic acid ester. By carbonylation in the presence of water or an alcohol pentenoic acid or an ester thereof may be converted to adipic acid or an adipate ester. The use of GVL as starting material is environmentally advantageous, as GVL can be made from renewable sources.

It has been known for a long time to prepare GVL from levulinic acid. U.S. Pat. No. 2,786,852 discloses a process for the preparation of GVL by passing a mixture of hydrogen and levulinic acid in the vapor phase over a copper oxide catalyst. The use of lower alkyl levulinate ester, in particular ethyl levulinate ester, is disclosed in U.S. Pat. No. 4,420,622, describing a process for the production of valerolactones from such esters and hydrogen in the presence of a solid particulate hydrogenation catalyst that contains a metal from Group VIII or Group Ib of the Periodic Table of Elements. The use of cobalt, nickel and copper on silica, magnesium oxide or chromium oxide is explicitly disclosed. Examples in U.S. Pat. No. 4,420,622 show that the use of levulinic acid instead of levulinate ester results in a fast deactivation of the catalyst. Both prior art processes are conducted in the gas phase. This entails that the reactor size is relatively large. Moreover, temperature control may be complicated and thermal gradient may be difficult to control. This all adds to the costs of such a gas phase process.

U.S. Pat. No. 6,617,464 discloses a process wherein levulinic acid and hydrogen are contacted with a catalyst that contains a Group VIII element, i.e. Groups 8-10, of the Periodic Table of Elements, in particular Ir, Pd, Pt, Re, Rh and Ru. The catalyst further contains a carrier, such as silica, titania, alumina and carbon. It may further contain a promoter, selected from another Group VIII metal or a Group Ib (Group 11) metal. The most preferred catalyst is ruthenium on carbon. The reaction is carried out in the liquid phase. The liquid phase is accomplished by dissolving levulinic acid in a suitable solvent, such as dioxane or 5-valerolactone.

The process according to U.S. Pat. No. 8,598,303 also employs levulinic acid as starting material and ruthenium on carbon as catalyst. The process is conducted in the presence of water, viz. up to 10% wt, based on the amount of levulinic acid. In U.S. Pat. No. 8,598,372 a gas phase reaction is described wherein levulinic acid is converted into GVL with hydrogen over a supported copper catalyst.

A supported copper catalyst was also used in the process described in U.S. Pat. No. 8,975,421. In this case levulinic acid was dissolved in water or methanol, or methyl levulinate was dissolved in methanol and reacted with hydrogen over a catalyst comprising copper on zirconia or copper on alumina. Especially the presence of levulinic acid and water caused significant metal leaching, and thus loss of catalytic activity.

In JP2014-166604 a process is described wherein levulinic acid or an ester thereof is contacted with hydrogen and a catalyst comprising copper oxide, zinc oxide and/or aluminum oxide. In this process the levulinic acid compound is in the gaseous phase, as it is believed that the hydrogenation of levulinic acid in the liquid phase requires high temperatures and noble metal-containing catalysts.

The influence of the catalyst support on the reaction between levulinic acid and hydrogen to GVL over a supported catalyst is described in US 2011/0046399. In this document a process is described wherein levulinic acid is contacted with a catalyst comprising one or more hydrogenation metals, such as those from Groups 8 to 10 of the Periodic Table of Elements, supported on titania or zirconia as carrier. These carriers provide more active catalysts than those which comprise silica or carbon as carrier. The levulinic acid is brought in the liquid phase by adjusting the reaction temperature and pressure. Although the description suggests that esters of levulinic acid can also be used, no proof thereof has been provided.

Another example of a process for the reaction of levulinic acid with hydrogen over a supported nickel catalyst is described in J. Lv et al., RSC Adv., 2015, 5, 72037. In this process levulinic acid is reacted with hydrogen in an autoclave in the presence of isopropanol as solvent. The support appears to have a significant influence on the conversion of the levulinic acid. Silica, alumina, titania, zirconia, zinc oxide and magnesium oxide were tested, wherein magnesium oxide as support shows the best effect. The highest conversion obtained in this batch process was 58.1% after two hours.

In U.S. Pat. No. 8,003,818 a process is disclosed wherein catalysts comprising a zeolite and a silica binder as support were compared with similar catalysts that did only contain silica as support. As hydrogenating metal component the catalyst may contain a variety of metals, in particular Groups 8 to 10 metals, such as nickel, rhodium, palladium, platinum, ruthenium, rhenium or combinations thereof. The catalysts were compared in the reaction of ethyl levulinate with hydrogen. It appeared that the catalysts that contained only silica as carrier produced certain amounts of GVL, whereas the catalysts that additionally contained a zeolite promoted the yield of pentenoate and pentanoate esters. This prior art document suggests that the presence of acidic groups may be detrimental to the yield of GVL.

Levulinate esters may also be converted into GVL by not using hydrogen as hydrogen donor, but by using an alcohol, such as isopropanol or 2-butanol as hydrogen donor. A metal oxide catalyst may be used. Such catalysts, such as zirconia, alumina, magnesia or titania convert the levulinate esters to GVL in the presence of the alcohol hydrogen donor. The basic sites on the solid catalysts may cause the formation of by-products such as condensation products. Such a reaction has e.g. been described in US 2012/0302764. This document also discloses the conversion of levulinic acid with hydrogen over a catalyst that comprises ruthenium as hydrogenating metal, tin as dopant and carbon as carrier. In US2007/0208183 another process is described wherein formic acid is used as hydrogen donor for the reaction of levulinate ester to GVL. The catalyst used can be a hydrogenating metal, such as nickel, on silica. The patent application describes that the reaction is preferably conducted in the gas phase. The process may be conducted batch-wise or continuously.

From the description of the prior art it is apparent that for the production of GVL from levulinic acid or from an ester thereof a variety of catalytically active metals can be used, and that the support that is used in the catalyst may have an influence on the catalytic activity. Further, the reaction may be conducted in the gas phase or the liquid phase, wherein the liquid phase may be provided by the use of a solvent or the application of suitable temperature and pressure. Moreover, an alcohol, formic acid or a hydrogen-containing gas may be used as hydrogen donor. When the process employs a levulinate ester as starting material, the prior art mainly discloses batch processes, which are less preferred than continuous processes.

SUMMARY OF THE INVENTION

The present inventors have found that the conversion into GVL is suitably conducted using a levulinic acid ester as starting material, wherein the reaction is conducted in the liquid phase and wherein the catalyst support comprises an oxide. The process is conducted as a continuous process. These reaction conditions enable to skilled person to obtain a commercially attractive process with high conversions. Accordingly, the present invention provides a continuous process for the preparation of gamma-valerolactone (GVL) from a levulinic acid ester by contacting a stream of the levulinic acid ester together with a gaseous stream of a hydrogen-containing gas with a hydrogenation catalyst, wherein the levulinic acid ester is in the liquid phase, and wherein the hydrogenation catalyst is a solid particulate catalyst comprising at least one hydrogenating metal or metal compound, supported on an oxide carrier.

DETAILED DESCRIPTION OF THE INVENTION

It has been found that the use of an oxide carrier has advantages over the use of a carbon carrier. Such carbon carriers have a tendency to become compact which leads to reduced surface areas and high pressure drops. Further, entrainment of fines frequently occurs when carbon-supported catalysts are used in continuous flow processes. Carbon-supported catalysts are also more fragile than metal oxide-supported catalysts. This is e.g. shown in U.S. Pat. No. 7,935,834, relating to a process for the hydrogenation of maleic acid to 1,4-butanediol, wherein it is disclosed that a common disadvantage of the use of a carbon support is that carbon fines are often generated during commercial operations. The generation of such fines can be minimized but generally cannot be completely avoided. During the hydrogenation process, such particulates can plug the void spaces in the catalyst through which the reactants must flow and thereby cause interruptions in the process. It further states that carbon supports may flake. Flaking or breaking of the carbon support can cause a higher pressure differential because the pores or void spaces in the catalyst are blocked so that the hydrogenatable precursor feed cannot pass through effectively. This can lead to crushing of the catalyst. It is thus evident that the use of an oxide carrier entails significant advantages.

Further, the liquid phase reaction avoids the use of large equipment. The use of a levulinic acid ester has advantages over the use of levulinic acid itself in that no acidic groups are present that may promote the formation of by-products. Thereby the selectivity of the reaction towards GVL formation is enhanced. Further, levulinic acid esters are less aggressive towards supports. Whereas levulinic acid may yield the unsaturated *angelica* lactone, which may lead to coke formation, the use of levulinate ester avoids the formation of *angelica* lactone, so that there is less risk of coke formation on the hydrogenation catalyst. Metal leaching has been observed when water or carboxylic acid is present. When a reaction mixture containing levulinic acid is maintained at elevated temperature leaching of metals from metal-supported catalysts may occur. The conversion of levulinic acid results in the formation of water and thus the risk of metal leaching is enhanced. Such risk may be avoided by using an ester as starting material. The application of a continuous process makes the reaction economically feasible. Moreover, by the use of a levulinic acid ester the deactivation of the catalyst is significantly reduced so that the continuous mode has become possible. Any detrimental compound that is formed, such as the alcohol that may cause leaching of the hydrogenating metal, can easily be removed continuously with the stream of hydrogen-containing gas.

The oxide carrier may be selected from a variety of supports and include metal oxides and silicon oxide carriers. In order to obtain the most attractive catalyst the selection of the most suitable hydrogenating metal as catalytically active component may play an important role, in addition to a selection of the most suitable carrier. It has been found that the hydrogenating metal in the hydrogenation catalyst is suitably selected from the group consisting of one or more of the metals of Groups 8 to 11 of the Periodic Table of the Elements.

The starting material in the process according to the present invention is a levulinic acid ester. Suitably, the ester is an alkyl levulinate, more preferably an alkyl levulinate wherein the alkyl group has 1 to 8 carbon atoms. More preferably, the levulinic acid ester is methyl levulinate, ethyl levulinate or a combination thereof. In the process of the present invention the levulinic acid ester is converted into GVL with the liberation of an alcohol. The use of the methyl and/or ethyl esters ensures that the alcohol that is liberated during the reaction can be easily removed with the stream of hydrogen-containing gas.

Hydrogen is used as another reactant. The hydrogen is supplied in the form of a hydrogen-containing gas. The hydrogen-containing gas may consist of hydrogen, but it is also feasible to supply hydrogen in the form of a gas wherein, in addition to hydrogen, also other gases are present. Such other gases may be selected from inert gases such as nitrogen, helium, neon, argon or combinations thereof. Although water vapor is not usually used, it is not necessary to severely dry the hydrogen-containing gas. The use of a hydrogen-containing gas that also comprises water vapor is not preferred, in order to avoid the risk of saponification of the levulinic acid ester. If hydrogen is supplied in the form of a hydrogen-containing gas, the proportion of hydrogen in the hydrogen-containing gas is suitably in the range of 20 to 100% vol, more preferably from 50 to 100% vol, based on the volume of the hydrogen-containing gas.

The reaction is conducted in the form of a liquid phase reaction. That means that the stream of levulinic acid ester is in the liquid phase. Preferably, the liquid phase is achieved by applying the appropriate reaction conditions, in particular appropriate temperature and pressure. The temperature and pressure may establish that the starting material, i.e. the levulinic acid ester, and the eventual products, in particular GVL, are in the liquid phase. Typically, the reaction conditions are such that hydrogen gas is dissolved in the liquid phase and the reaction takes place in the liquid phase. It is assumed that the reaction is catalyzed on the solid surface of the catalyst. Advantageously, the process is conducted in the substantial absence of solvent. If no solvent is to be used the isolation of the products is facilitated. Therefore, the reaction is suitably conducted in the substantial absence of a solvent. This represents a significant advantage in the work-up of the product now that no solvent is to be removed from the products. Moreover, there is no risk for solvent losses during the process.

The reaction is suitably conducted at a temperature in the range of 75 to 400° C., preferably from 125 to 300° C. The total pressure of the reaction mixture is selected such that the reaction mixture is in the liquid phase. The total pressure of the reaction mixture is therefore suitably in the range from 2 to 100 bar. As indicated above, it is not required that the total pressure is achieved by hydrogen alone. Still, in order to ensure that the reaction proceeds smoothly, the amount of hydrogen is suitably provided in excess of the stoichiometric need. Therefore, the hydrogen partial pressure may be in the range of 2 to 100 bar, with a preference for a hydrogen partial pressure in the range of 5 to 80 bar.

It has been found that since the formation of by-products is reduced when a levulinic acid ester is used as starting material, the contact time of the starting material may vary within wide ranges. When the hydrogenation catalyst is very active, the contact time may be very short. The weight hourly space velocity is therefore preferably in the range of 0.1 to 1000 kg levulinic acid ester per kg catalyst per hour, more preferably from 1 to 100 $h^{-1}$.

As indicated above, the selection of the hydrogenation metal may play a role in the activity and stability of the hydrogenation catalyst. The hydrogenation metal can suitably be selected from the Groups 8 to 10 metals iron, cobalt and nickel. Preferably, the hydrogenation metal is nickel. The nickel-containing catalyst may further contain one or more dopants. By dopant is understood a minor component, such as in an amount of up to 20% wt, based on the oxide carrier. One suitable dopant is a platinum group metal. By platinum group metal is understood any of the six elements Ru, Rh, Pd, Os, Ir and Pt. Since Os tends to be unstable, the use of the other five elements is preferred. The dopant is preferably platinum or palladium, more preferably platinum. The amount of nickel is suitably in the range of 1 to 75% wt, calculated as metal and based on the hydrogenation catalyst. Preferably, the amount of nickel is in the range of 10 to 40% wt. The dopant may be present in a small amount. When a dopant is present, the amount thereof is suitably in the range of 0.01 to 0.5% wt, calculated as metal and based on the hydrogenation catalyst. The carrier may be selected from a variety of oxide carriers. Suitable carriers include silica, alumina, silica-alumina, titania, zirconia, magnesia, ceria, chromia and mixtures thereof. Since it has been found that the use of alumina as carrier advantageously results in a greater activity and stability of the nickel-containing catalysts over the use of silica, the oxide carrier comprises suitably alumina. It has further been found that nickel-containing catalysts in the process of the present invention perform very well when the reaction temperature is in the range of 125 to 200° C. Hence, the reaction temperature is preferably in this range when a nickel-containing catalyst is used.

Alternatively, a hydrogenation catalyst can be used in the present process which comprises copper from Group 11 as hydrogenating metal. The hydrogenation catalyst may comprise copper as sole hydrogenating metal. The hydrogenation catalyst may also comprise other metals as dopants. Such dopants can be selected from a variety of non-noble metals. An advantageous dopant is zinc. The copper-containing catalyst suitably comprises copper in an amount in the range of 1 to 75% wt, calculated as metal and based on the hydrogenation catalyst. Preferably, the amount of copper is in the range of 30 to 70% wt, calculated as metal and based on the hydrogenation catalyst. When zinc is present as dopant, the amount of zinc may range from 1 to 40% wt, calculated as metal and based on the hydrogenation catalyst. It is understood that although the amounts of copper and zinc may vary between these wide ranges, the amounts will be such that the hydrogenation catalyst comprises at least 25% wt of oxide carrier, the percentage being based on the hydrogenation catalyst. The oxide carrier may be selected from a variety of oxides, including silica, alumina, magnesia, zirconia, chromia, ceria and combinations thereof. Advantageously, the oxide carrier is selected from silica or alumina, preferably alumina. The reaction temperature may be relatively high; viz. in the range of 150 to 300° C. It has been found that any activity loss from which the catalyst may suffer during the course of the process, can be compensated by increasing the reaction temperature. Further, it has been found that catalysts comprising copper and zinc as dopant and alumina or silica or a combination thereof as carrier are very stable. The activity of such catalysts does not decrease over time, so that a very active catalyst is still in operation after a considerable time on stream. Hence, such catalyst are especially preferred, in particular those that comprise alumina as carrier.

In a third embodiment the hydrogenating metal in the hydrogenation catalyst may be selected from a platinum group metal. In such a case, the hydrogenation catalyst preferably comprises in addition tin or a tin compound as dopant. The platinum group metal can be selected from the six elements mentioned above, i.e. Ru, Rh, Pd, Os, Ir and Pt, in particular Ru, Rh, Pd, Ir and Pt. It is also possible to use combinations of such metals. It is surprising that tin may act as a dopant, as the addition of other metals in the hydrogenation catalyst result in a deterioration of the performance thereof. The amount of platinum group metal in the hydrogenation catalyst is suitably selected from the range of 0.2 to 7.5% wt, calculated as metal and based on the hydrogenation catalyst. When tin is present as dopant, it is preferably present in an amount in the range of 20 to 200% wt, calculated as metal and based on the platinum-group metal. It has been found that the amount of tin preferably is selected such that the atomic ratio of tin to platinum-group metal is in the range of 0.1 to 1.4, more preferably from 0.25 to 1.25, and most preferably from 0.75 to 1.1. In certain embodiments the use of an equimolar amount of tin and the platinum-group metal is advantageous.

The preparation of the catalysts that are used in the process of the present invention is known to the skilled person. When the hydrogenation catalyst comprises a platinum group metal, it is known to impregnate the oxide carrier with a solution of a salt or acid of the platinum group metal.

Examples of such salts or acids are tetra-amine platinum nitrate and dihydrogen hexachloro platinate. After impregnation, the impregnated carriers are calcined, typically at a temperature in the range of 250 to 500° C., such as about 275 to 400° C. The calcination may be performed in an inert atmosphere, such as under nitrogen. However, the calcination is suitably carried out in an oxygen-containing atmosphere, such as air. The duration of the calcination may vary from about 1 hour to about 24 hours, preferably from 2 to 20 hours, more preferably from 5 to 15 hours. It has been found that calcination may have an effect on the catalyst activity. Especially when the calcination is carried out for too long a period, the activity of the catalyst may deteriorate. That also applies to calcination temperatures. When the calcination temperature becomes too high, e.g. from 450° C. and higher, the effectiveness of the resulting catalyst tends to decrease. That applies in particular to catalysts that comprise both a platinum group metal and a tin dopant. Subsequently, the calcined carriers are subjected to reduction and activation by treating them with hydrogen at a temperature in the range of 250 to 300° C. It has surprisingly been found that the use of dihydrogen hexachloro platinate yields more active catalysts. Whereas in many cases the presence of any chloride residues on a catalyst may lead to a deteriorated performance, it is surprising that when the catalyst is produced from a chlorine-containing precursor very active catalysts are obtained. This is especially the case, when the preparation of the catalyst involves the simultaneous impregnation of a salt or acid of the platinum group metal and a salt of tin, such as tin(II) chloride or tin(II)tartrate.

The oxide carrier suitably comprises one or more of silicon oxide and metal oxides. These metal oxides are typically selected from aluminum oxide, zirconium oxide, titanium oxide, cerium oxide, chromium oxide and combinations thereof. The metal oxides may comprise other metal oxides as dopants, i.e., as minor components, such as in an amount of up to 20% wt, based on the oxide carrier. Such other oxides may be selected from magnesium oxide, calcium oxide, barium oxide, zinc oxide and combinations thereof. The oxide carrier advantageously contains an alkali metal dopant. The presence of the alkali metal dopant results in a modified carrier that has a modified performance. Especially when the oxide carrier comprises alumina, silica, zirconia, titania and mixtures thereof, the activity of the resulting hydrogenation catalyst is enhanced. It is very surprising that the presence of an alkali metal in the carrier has such an activity-enhancing effect on the resulting catalyst.

The alkali metal can typically be selected from lithium, sodium, potassium, rubidium or cesium. Preferably, the alkali metal is sodium or potassium, more preferably potassium. The amount of alkali metal in the oxide carrier is suitably in the range of 0.2 to 10% wt, calculated as metal oxide and based on the oxide carrier. The carrier is typically prepared by impregnating the oxide carrier with a solution of alkali metal hydroxide, followed by drying and calcination in air.

The GVL product of the process of the invention can be used in a number of applications. Due to its pleasant odor it may be used as solvent or fragrance. It may also be used a starting material for polymers; since it is obtainable from biomass it is considered a sustainable source and polymers made from GVL may replace fossil fuel-based polymers. It may be further hydrogenated to produce valeric acid or transesterified to produce ethyl pentenoate according to the procedures described in WO 2006/067171 and WO 2005/058793. In one embodiment, hydrogenation according to the present invention to produce GVL and the subsequent hydrogenation or transesterification step may suitably be carried out in a single reactor. Evidently, any reactor constellation may be used in the further treatment of GVL.

The present invention will be further illustrated by means of the following examples.

EXAMPLE 1

Five nickel-containing hydrogenation catalysts were tested. The catalysts were loaded into a tubular reactor. The catalysts were reduced to ensure that nickel was in its metal form using hydrogen at temperatures in the range of 180 to 340° C.

Subsequently, methyl levulinate was passed over the catalyst bed. Simultaneously, a stream of a hydrogen-containing gas, consisting for 95% vol of $H_2$, was passed over the bed of catalyst. This resulted in a particular molar ratio between hydrogen and methyl levulinate (ML). The total pressure in the reactor at the reaction temperature was 40 bar. The effluent of the reactor was analyzed.

Methyl levulinate conversion was based on the amount of ML that was introduced into the reactor. The selectivity of the reactions to GVL was virtually 100%.

The Table 1 below shows the composition of the catalyst wherein the amount of nickel and dopant are expressed in % wt, based on the total catalyst. The table also mentions the oxide carrier, the molar ratio of $H_2$/ML, the time on stream, and the ML conversion at the indicated time on stream. The table also shows the space time yield (STY), expressed in gram GVL/gram catalyst/hour, calculated as the amount of ML (in moles) introduced into the reactor times the ML conversion times the molecular weight of GVL.

TABLE 1

| Exp. No. | Catalyst No. | Ni, % wt | Dopant, % wt | Oxide carrier | T, ° C. | $H_2$/ML, mol/mol | Time on stream, h | ML conversion, % | STY |
|---|---|---|---|---|---|---|---|---|---|
| 1 | 1 | 55 | — | $SiO_2$ | 150 | 4.7 | 50 | 53.0 | 7.1 |
| 2 | 2 | 5 | Pt, 0.05 | $SiO_2$ | 150 | 4.8 | 18 | 28.5 | 0.9 |
| 3 | 3 | 5 | — | $Al_2O_3$ | 210 | 4.5 | 150 | 12.8 | 0.2 |
| 4 | 4 | 24 | — | $Al_2O_3$ | 150 | 4.7 | 68 | 99.9 | 3.6 |
| 5 | 5 | 27 | — | $Al_2O_3$ | 170 | 5.3 | 180 | 99.7 | 27.3 |

EXAMPLE 2

In a similar way as shown in Example 1 four copper-containing catalysts were tested. Also these copper-containing hydrogenation catalysts were reduced by hydrogen to bring them into their metal form. ML was introduced into the reactor simultaneously with the hydrogen-containing gas stream. The reaction pressure was 40 bar. Table 2 shows the catalyst compositions, the reaction temperature, the molar ratio of $H_2$ to ML, the time on stream, the ML conversion and the space time yield.

TABLE 2

| Exp. No. | Catalyst No. | Cu, % wt | Dopant, % wt | Oxide carrier | T, °C. | H₂/ML, mol/mol | Time on stream, h | ML conversion, % | STY |
|---|---|---|---|---|---|---|---|---|---|
| 6 | 6 | 5 | — | TiO₂ | 190 | 4.6 | 83 | 13.4 | 0.5 |
| 7 | 7 | 5 | — | ZrO₂ | 170 | 9.3 | 3.4 | 99.9 | 15.4 |
| 8 | 7 | 5 | — | ZrO₂ | 170 | 9.4 | 137 | 34 | 5.3 |
| 9 | 8 | 62 | — | SiO₂ | 190 | 9.8 | 182 | 99.9 | 17.5 |
| 10 | 9 | 41 | Zn, 26 | Al₂O₃ | 170 | 9.3 | 3.1 | 99.9 | 21.2 |
| 11 | 9 | 41 | Zn, 26 | Al₂O₃ | 250 | 4.7 | 259 | 99.3 | 11.6 |

From the experiments it is apparent that all catalysts are active. Catalyst 7 is somewhat less stable compared with catalysts 8 and 9, which are still very active after a considerable time on stream. Catalyst 9 is particularly stable.

EXAMPLE 3

The suitability of noble metals as hydrogenating metals in the present process was tested in a number of experiments that were conducted in the same way as described for Example 1. The reaction temperature in all experiments was 190° C. and the H₂/ML molar ratio in all experiments was 4.6 mole/mole.

The catalysts consisted of the noble metal, as indicated in Table 3 and the carrier. No dopant was present. The results are shown in Table 3.

For comparison reasons a number of comparative catalysts were tested under the same conditions as described for the experiments Nos. 12-27. The catalytically active metals were supported on an active carbon carrier. The results are shown in Table 4.

TABLE 3

| Exp. No. | Catalyst No. | Noble metal, % wt | Oxide carrier | Time on stream, h | ML conversion, % | STY |
|---|---|---|---|---|---|---|
| 12 | 10 | Pt, 0.26 | ZrO₂ | 80 | 31.2 | 0.5 |
| 13 | 11 | Pt, 5 | TiO₂ | 85 | 22.7 | 3.6 |
| 14 | 12 | Pt, 1 | ZrO₂ | 79 | 23 | 0.74 |
| 15 | 13 | Pt, 5 | SiO₂—Al₂O₃ | 77 | 34.4 | 2.8 |
| 16 | 14 | Ru, 1 | ZrO₂ | 70 | 98.6 | 0.5 |
| 17 | 15 | Ru, 2.1 | ZrO₂ | 87 | 94.0 | 1.05 |
| 18 | 16 | Ru, 1 | TiO₂ | 70 | 81.7 | 0.4 |
| 19 | 17 | Pt, 0.5 | Al₂O₃ | 76 | 17.3 | 0.1 |
| 20 | 18 | Pt, 0.2 | TiO₂ | 78 | 2.8 | <0.1 |
| 21 | 19 | Au, 1 | CeO₂—ZrO₂ | 74 | 26.4 | 0.1 |
| 22 | 20 | Pd, 0.2 | TiO₂ | 73 | 1.5 | <0.1 |
| 23 | 21 | Pt, 1 | SiO₂ | 75 | 4.3 | 0.1 |
| 24 | 22 | Pd, 1 | TiO₂ | 74 | 2.1 | <0.1 |
| 25 | 23 | Pt, 5 | Al₂O₃ | 76 | 0.9 | 0.1 |
| 26 | 24 | Pt, 1 | CeO₂ | 80 | 1.3 | <0.1 |
| 27 | 25 | Pt, 1 | Al₂O₃ | 76 | 0.1 | <0.1 |

TABLE 4

| Exp. No. | Catalyst No. | Noble metal, % wt | Carrier | Time on stream, h | ML conversion, % | STY |
|---|---|---|---|---|---|---|
| 28 | 26 | Ru, 1 | C | 69 | 24.9 | 0.4 |
| 29 | 27 | Ru, 3 | C | 70 | 58.4 | 1.3 |
| 30 | 28 | Pt, 0.5 | C | 75 | 2.3 | <0.1 |

Comparisons between experiment Nos. 18 and 28 and between experiment Nos. 19 and 30 show that the use of oxide carriers in the present process leads to more favorable results.

EXAMPLE 4

To show the beneficial effect of the use of tin dopants a number of tin-containing platinum hydrogenation catalysts were tested and compared with similar catalysts that did not contain tin. The experiments were conducted in a similar way as described for Example 1 at a WHSV of 18 h⁻¹. The pressure was 40 bar, the H₂/ML ratio was 9.4 mol/mol, and the reaction temperature was 130° C. The amount of tin was set to be equimolar with the amount of platinum. Table 5 also indicates the amount of tin in the catalyst.

TABLE 5

| Exp. No. | Catalyst No. | Pt, % wt | Sn, % wt | Oxide carrier | Time on stream, h | ML conversion, % | STY |
|---|---|---|---|---|---|---|---|
| 31 | 29 | 2 | — | Al₂O₃ | 100 | 5.4 | 0.8 |
| 32 | 30 | 2 | 1.2 | Al₂O₃ | 98 | 49.9 | 7.1 |
| 33 | 31 | 2 | — | SiO₂ | 100 | 2.7 | 0.4 |
| 34 | 32 | 2 | 1.2 | SiO₂ | 98 | 17.1 | 2.5 |
| 35 | 33 | 2 | — | SiO₂—Al₂O₃ | 101 | 6.6 | 1.0 |
| 36 | 34 | 2 | 1.2 | SiO₂—Al₂O₃ | 99 | 7.5 | 1.1 |
| 37 | 35 | 2 | — | SiO₂—TiO₂ | 101 | 4.4 | 0.7 |
| 38 | 36 | 2 | 1.2 | SiO₂—TiO₂ | 99 | 68.2 | 9.7 |
| 39 | 37 | 2 | — | SiO₂—ZrO₂ | 102 | 0.1 | 0.0 |
| 40 | 38 | 2 | 1.2 | SiO₂—ZrO₂ | 100 | 5.5 | 0.8 |

TABLE 5-continued

| Exp. No. | Catalyst No. | Pt, % wt | Sn, % wt | Oxide carrier | Time on stream, h | ML conversion, % | STY |
|---|---|---|---|---|---|---|---|
| 41 | 39 | 2 | — | $TiO_2$ | 100 | 45.3 | 6.3 |
| 42 | 40 | 2 | 1.2 | $TiO_2$ | 99 | 65.9 | 9.1 |
| 43 | 41 | 2 | — | $ZrO_2$ | 101 | 5.2 | 0.8 |
| 44 | 42 | 2 | 1.2 | $ZrO_2$ | 98 | 72.1 | 10.0 |

In addition, two more experiments were conducted with different tin- and platinum-containing catalysts at higher temperatures, viz. 190° C., and at a $H_2$/ML molar ratio of 4.6. The performances of these catalysts were compared with that of catalyst No. 21. The results are shown in Table 6. Moreover, three other catalysts, being modifications of catalyst 31, were tested. These three catalysts also had varying amounts of tin. These catalysts were tested at a reaction temperature of 150° C. Also the results of these experiments are shown in Table 6.

TABLE 6

| Exp. No. | Catalyst No. | Pt, % wt | Sn, % wt | T, ° C. | $H_2$/ML, m/m | Oxide carrier | Time on stream, h | ML conversion, % | STY |
|---|---|---|---|---|---|---|---|---|---|
| 45 | 21 | 1 | — | 190 | 4.6 | $SiO_2$ | 75 | 4.3 | 0.1 |
| 46 | 43 | 1 | 0.46 | 190 | 4.6 | $SiO_2$ | 81 | 99.5 | 6.5 |
| 47 | 44 | 1 | 0.91 | 190 | 4.6 | $SiO_2$ | 82 | 94.3 | 5.9 |
| 48 | 31 | 2 | — | 150 | 9.4 | $SiO_2$ | 145 | 9.0 | 1.3 |
| 49 | 45 | 1 | 0.37 | 150 | 9.4 | $SiO_2$ | 155 | 61.4 | 9.0 |
| 50 | 46 | 1 | 0.49 | 150 | 9.4 | $SiO_2$ | 156 | 51.8 | 7.6 |
| 51 | 47 | 1 | 0.61 | 150 | 9.4 | $SiO_2$ | 142 | 36.6 | 5.4 |
| 52 | 48 | 1 | 0.73 | 150 | 9.4 | $SiO_2$ | 156 | 25.1 | 3.7 |

For comparison reasons some other metals were used as dopants. The resulting hydrogenation catalysts were compared with catalyst No. 31. The experiments were conducted under the conditions of the other experiments of this example 4, the alterations being a reaction temperature of 150° C. and a $H_2$/ML ratio of 9.3. The other metals were also present in a 1:1 molar ratio with platinum. The results are shown in Table 7.

TABLE 7

| Exp. No. | Catalyst No. | Pt, % wt | dopant, % wt | Oxide carrier | Time on stream, h | ML conversion, % | STY |
|---|---|---|---|---|---|---|---|
| 53 | 31 | 2 | — | $SiO_2$ | 78 | 5.2 | 0.7 |
| 54 | 49 | 1 | Fe, 0.29 | $SiO_2$ | 88 | 1.9 | 0.3 |
| 55 | 50 | 1 | Pb, 1.06 | $SiO_2$ | 88 | 0.1 | 0.0 |
| 56 | 51 | 1 | Sb, 0.62 | $SiO_2$ | 88 | 0.2 | 0.0 |
| 57 | 47 | 1 | Sn, 0.61 | $SiO_2$ | 75 | 80.1 | 11.8 |

The results of experiment Nos. 53 to 57 show that tin has a very favorable effect on the activity of the resulting catalyst, whereas other metals appear to lead to a detrimental performance of the catalysts.

EXAMPLE 5

To show the effect of oxide carriers that contain an alkali metal, a series of experiments was carried out in a similar way as described for the other examples. The reaction temperature was set at 130° C., the $H_2$/ML molar ratio was 9.4. The WHSV in all experiments was 18 h$^{-1}$. All catalysts used contained platinum and tin. The carriers that contained an alkali metal were impregnated with potassium hydroxide solution, followed by drying and calcination, prior to impregnation with the platinum and tin compounds. The amount of potassium was 2% wt, calculated as elemental potassium and based on the carrier. The results are shown in Table 8.

In a second series of experiments the amounts of tin in the catalysts were varied. The experiments were further carried out at different reaction temperatures and different $H_2$/ML molar ratios. All carriers contained 2% wt of potassium. The results are shown in Table 9.

TABLE 8

| Exp. No. | Catalyst No. | Pt, % wt | Sn, % wt | Oxide carrier | K carrier, % wt | Time on stream, h | ML conversion, % | STY |
|---|---|---|---|---|---|---|---|---|
| 32 | 30 | 2 | 1.2 | $Al_2O_3$ | — | 98 | 49.9 | 7.1 |
| 58 | 48 | 2 | 1.2 | $Al_2O_3$ | 2 | 103 | 90.5 | 12.6 |
| 34 | 32 | 2 | 1.2 | $SiO_2$ | — | 98 | 17.1 | 2.5 |
| 59 | 49 | 2 | 1.2 | $SiO_2$ | 2 | 102 | 2.2 | 0.3 |
| 36 | 34 | 2 | 1.2 | $SiO_2$—$Al_2O_3$ | — | 99 | 7.5 | 1.1 |
| 60 | 50 | 2 | 1.2 | $SiO_2$—$Al_2O_3$ | 2 | 104 | 38.6 | 5.6 |
| 38 | 36 | 2 | 1.2 | $SiO_2$—$TiO_2$ | — | 99 | 68.2 | 9.7 |
| 61 | 51 | 2 | 1.2 | $SiO_2$—$TiO_2$ | 2 | 104 | 40.6 | 6.0 |

TABLE 8-continued

| Exp. No. | Catalyst No. | Pt, % wt | Sn, % wt | Oxide carrier | K carrier, % wt | Time on stream, h | ML conversion, % | STY |
|---|---|---|---|---|---|---|---|---|
| 40 | 38 | 2 | 1.2 | $SiO_2$—$ZrO_2$ | — | 100 | 5.5 | 0.8 |
| 62 | 52 | 2 | 1.2 | $SiO_2$—$ZrO_2$ | 2 | 105 | 56.1 | 8.0 |
| 42 | 40 | 2 | 1.2 | $TiO_2$ | — | 99 | 65.9 | 9.1 |
| 63 | 53 | 2 | 1.2 | $TiO_2$ | 2 | 95 | 68.2 | 9.7 |
| 44 | 42 | 2 | 1.2 | $ZrO_2$ | — | 98 | 72.1 | 10.0 |
| 64 | 54 | 2 | 1.2 | $ZrO_2$ | 2 | 104 | 83.8 | 12.1 |

TABLE 9

| Exp. No. | Cat. No. | Pt, % wt | Sn, % wt | Oxide carrier | T, °C. | $H_2$/ML, m/m | Time on stream, h | ML conv. % | STY |
|---|---|---|---|---|---|---|---|---|---|
| 65 | 54 | 2 | 1.2 | $ZrO_2$—K | 210 | 9.6 | 35 | 99.6 | 52.1 |
| 66 | 54 | 2 | 1.2 | $ZrO_2$—K | 190 | 12.6 | 246 | 95.2 | 532.4 |
| 67 | 55 | 2 | 0.6 | $ZrO_2$—K | 210 | 9.6 | 19 | 99.4 | 50.7 |
| 68 | 55 | 2 | 0.6 | $ZrO_2$—K | 190 | 12.6 | 253 | 91.7 | 49.2 |
| 69 | 52 | 2 | 1.2 | $SiO_2$—$ZrO_2$—K | 210 | 9.6 | 36 | 90.7 | 48.7 |
| 70 | 56 | 2 | 0.6 | $TiO_2$—K | 210 | 9.6 | 40 | 98.8 | 50.4 |
| 71 | 57 | 2 | 0.6 | $Al_2O_3$—K | 210 | 9.6 | 38 | 92.2 | 48.3 |
| 72 | 48 | 2 | 1.2 | $Al_2O_3$—K | 210 | 9.6 | 32 | 87.6 | 47.1 |
| 73 | 48 | 2 | 1.2 | $Al_2O_3$—K | 170 | 10 | 77 | 87.5 | 38.3 |
| 74 | 57 | 2 | 0.6 | $Al_2O_3$—K | 170 | 10 | 82 | 73.1 | 31.3 |
| 75 | 54 | 2 | 1.2 | $ZrO_2$—K | 170 | 10 | 79 | 91.0 | 38.2 |
| 76 | 55 | 2 | 0.6 | $ZrO_2$—K | 170 | 10 | 86 | 80.4 | 33.7 |
| 77 | 53 | 2 | 1.2 | $TiO_2$—K | 170 | 10 | 78 | 55.3 | 24.7 |
| 78 | 56 | 2 | 0.6 | $TiO_2$—K | 170 | 10 | 84 | 80.6 | 36.0 |

The results of experiment Nos. 66 and 68 show that the catalyst comprising a platinum-group metal, in particular platinum, and a tin dopant on a zirconia carrier that is doped with an alkali metal, in particular with potassium, show an excellent activity, also after a long time on stream. This indicates that such catalysts have excellent stability.

EXAMPLE 6

Two platinum-on-silica catalysts were prepared. In the first case silica was impregnated with an appropriate amount of an aqueous solution of tetraamine Pt(II) nitrate and tin(II) tartrate hydrate to obtain a catalyst comprising 1% wt of platinum and 0.46% wt of tin, based on the silica (catalyst 58). In the second case another sample of this silica was impregnated with an aqueous solution of dihydrogen hexachloro platinate(IV) and tin(II) dichloride to obtain another catalyst comprising 1% wt of platinum and 0.46% wt of tin, based on the silica (catalyst 59). Both catalysts were dried and then calcined at 350° C. for 4 hours. Subsequently, they were activated in-situ at 280° C. for 8 hours under a flow of 5% $H_2$ in $N_2$.

Both catalysts were used in experiments that were conducted in a similar way as described for Example 3. The reaction temperature was 170° C., the pressure was 40 bar, and the hydrogen/ML ratio was 5.3. Other conditions and the results are shown in Table 10.

TABLE 10

| Exp. No. | Cat. No. | Time on stream, h | ML conversion, % | STY |
|---|---|---|---|---|
| 79 | 58 | 182.5 | 43.4 | 6.3 |
| 80 | 59 | 183.2 | 97.6 | 14.4 |

EXAMPLE 7

To show the influence of calcinations conditions on the catalytic performance of eventual catalysts two identical catalyst compositions consisting of 2% wt of platinum and an equimolar amount of tin, based on the amount of platinum, were prepared by impregnation of silica with an aqueous solution of tetraamine Pt(II) nitrate and tin(II) tartrate hydrate. The catalysts were dried and calcined at different temperatures and during different periods. Then the catalysts were activated in-situ at 280° C. for 8 hours under a flow of 5% $H_2$ in $N_2$.

Subsequently, the calcined catalysts were used in a series of experiments that were conducted in a similar way as described for Example 1. In each experiment the molar ratio between hydrogen and methyl levulinate (ML) was 5.3, and the reaction temperature was 170° C. The effluents of the reactions were analyzed. The total pressure was 40 bar. The calcination conditions, the time on stream (TOS) and the ML conversion (ML cony.) at the measured time on stream for each experiment are shown in Table 11.

TABLE 11

| Exp. No. | Catalyst | Calcination T, °C. | Calcination time, h | TOS, h | ML conv., % |
|---|---|---|---|---|---|
| 81 | Pt/Sn/$SiO_2$ | 300 | 12 | 174 | 56.5 |
| 82 | Pt/Sn/$SiO_2$ | 300 | 4 | 174 | 10.6 |
| 83 | Pt/Sn/$SiO_2$ | 350 | 12 | 173 | 73.6 |
| 84 | Pt/Sn/$SiO_2$ | 350 | 4 | 173 | 59.1 |
| 85 | Pt/Sn/$SiO_2$ | 450 | 12 | 172 | 19.7 |
| 86 | Pt/Sn/$SiO_2$ | 450 | 4 | 172 | 17.6 |

The results show that a calcination for 4 hours is effective, but that an improvement is obtained when the calcination period is extended to 12 hours. The results further show that when the calcination temperature becomes too high, the effectiveness of the resulting catalyst decreases, after having reached maximum effectiveness.

The invention claimed is:

1. A continuous process for the preparation of gamma-valerolactone (GVL) from a levulinic acid ester comprising:
    contacting a stream of the levulinic acid ester together with a gaseous stream of a hydrogen-containing gas with a hydrogenation catalyst,
    wherein the levulinic acid ester is in the liquid phase,
    wherein the hydrogenation catalyst is a solid particulate catalyst comprising at least one hydrogenating metal, supported on an oxide carrier, and
    which is conducted in the absence of solvent.

2. The process according to claim 1, wherein the hydrogenating metal in the hydrogenation catalyst is selected from the group consisting of one or more of the metals of groups 8 to 11 of the Periodic Table of Elements.

3. The process according to claim 1, wherein the levulinic acid ester is an alkyl levulinate.

4. The process according to claim 1, which is conducted at a temperature in the range of 75 to 400° C.

5. The process according to claim 1, wherein the hydrogenation catalyst comprises nickel as hydrogenating metal.

6. The process according to claim 5, wherein the hydrogenation catalyst comprises nickel in an amount of 1 to 75% wt, calculated as metal and based on the hydrogenation catalyst.

7. The process according to claim 5, wherein the hydrogenation catalyst comprises a platinum-group metal as dopant.

8. The process according to claim 1, wherein the hydrogenation catalyst comprises copper as hydrogenating metal.

9. A continuous process for the preparation of gamma-valerolactone (GVL) from a levulinic acid ester comprising:
    contacting a stream of the levulinic acid ester together with a gaseous stream of a hydrogen-containing gas with a hydrogenation catalyst,
    wherein the levulinic acid ester is in the liquid phase,
    wherein the hydrogenation catalyst is a solid particulate catalyst comprising at least one hydrogenating metal, supported on an oxide carrier,
    wherein the hydrogenation catalyst comprises copper as hydrogenating metal, and
    wherein the hydrogenation catalyst comprises a zinc compound as dopant.

10. The process according to claim 9, wherein the hydrogenation catalyst comprises copper in an amount of 1 to 75% wt, calculated as metal and based on the hydrogenation catalyst.

11. A continuous process for the preparation of gamma-valerolactone (GVL) from a levulinic acid ester comprising:
    contacting a stream of the levulinic acid ester together with a gaseous stream of a hydrogen-containing gas with a hydrogenation catalyst,
    wherein the levulinic acid ester is in the liquid phase,
    wherein the hydrogenation catalyst is a solid particulate catalyst comprising at least one hydrogenating metal, supported on an oxide carrier, and
    wherein the hydrogenation catalyst comprises a platinum-group metal as hydrogenating metal and, optionally, tin or a tin compound as dopant.

12. The process according to claim 11, wherein the platinum group metal is platinum.

13. The process according to claim 11, wherein the hydrogenation catalyst comprises a platinum group metal in an amount of 0.1 to 7.5% wt, calculated as metal and based on the hydrogenation catalyst.

14. The process according to claim 11, wherein the hydrogenation catalyst comprises tin or a tin compound in an amount of 20 to 200% wt, calculated as metal and based on the platinum-group metal.

15. The process according to claim 9, wherein the oxide carrier contains an alkali metal.

16. The process according to claim 15, wherein the alkali metal is potassium.

17. The process according to claim 15, wherein the amount of alkali metal is in the range of 0.2 to 10% wt, calculated as element and based on the oxide carrier.

18. The process according to claim 11, wherein the oxide carrier is selected from the group consisting of alumina, silica, zirconia, titania and mixtures thereof.

19. The process according to claim 5, wherein the hydrogenation catalyst is supported on a carrier of aluminum oxide.

* * * * *